United States Patent
Graziani et al.

(10) Patent No.: US 12,295,631 B2
(45) Date of Patent: May 13, 2025

(54) GUIDED SYSTEMS AND METHODS FOR IMPLANTING FASTENERS INTO TISSUE

(71) Applicant: Spinedust SAS, Marseilles (FR)

(72) Inventors: Noel Graziani, Marseilles (FR); Olivier Levrier, Marseilles (FR)

(73) Assignee: Spinedust SAS (FR)

( * ) Notice: Subject to any disclaimer, the term of this patent is extended or adjusted under 35 U.S.C. 154(b) by 370 days.

(21) Appl. No.: 17/729,964

(22) Filed: Apr. 26, 2022

(65) Prior Publication Data
US 2023/0338074 A1      Oct. 26, 2023

(51) Int. Cl.
| | |
|---|---|
| *A61B 17/88* | (2006.01) |
| *A61B 17/90* | (2006.01) |
| *A61B 34/30* | (2016.01) |
| *A61B 90/50* | (2016.01) |
| *A61B 17/56* | (2006.01) |
| *A61B 90/00* | (2016.01) |

(52) U.S. Cl.
CPC .......... *A61B 17/8875* (2013.01); *A61B 17/90* (2021.08); *A61B 34/30* (2016.02); *A61B 90/50* (2016.02); *A61B 2017/564* (2013.01); *A61B 2090/0807* (2016.02)

(58) Field of Classification Search
CPC ............ A61B 17/7032; A61B 17/1757; A61B 17/7082; A61B 17/864; A61B 17/8875; A61B 17/90; A61B 2017/564; A61B 17/8897
See application file for complete search history.

(56) References Cited

U.S. PATENT DOCUMENTS

| | | | |
|---|---|---|---|
| 2020/0229881 A1* | 7/2020 | Leboeuf, II | A61B 34/30 |
| 2021/0212701 A1* | 7/2021 | Khosla | A61B 17/1615 |
| 2022/0061895 A1* | 3/2022 | Kibrya | A61B 17/8897 |

* cited by examiner

*Primary Examiner* — Samuel S Hanna
(74) *Attorney, Agent, or Firm* — Farber LLC

(57) ABSTRACT

Systems, devices and methods are provided for implanting screws into tissue, such as bone. A system comprises a screwdriver having a central shaft with a longitudinal axis and a distal end configured for attachment to a screw and an inner lumen for receiving a guidewire. The device further includes a retaining device for holding the guidewire fixed relative to the screw as the screw is advanced in a distal direction and a release device for releasing the guidewire from the screw and holding the guidewire fixed relative to the longitudinal axis as the screw is advanced in the distal direction. This allows a physician to advance a guidewire in front of the screw to more accurately follow a desired screwing axis, and to minimize trauma during tightening of the screw into the tissue. In addition, the guidewire can be released from the screw during implantation such that the guidewire no longer advances with the screw, thereby limiting distal movement of the guidewire and minimizing damage to surrounding tissue.

28 Claims, 16 Drawing Sheets

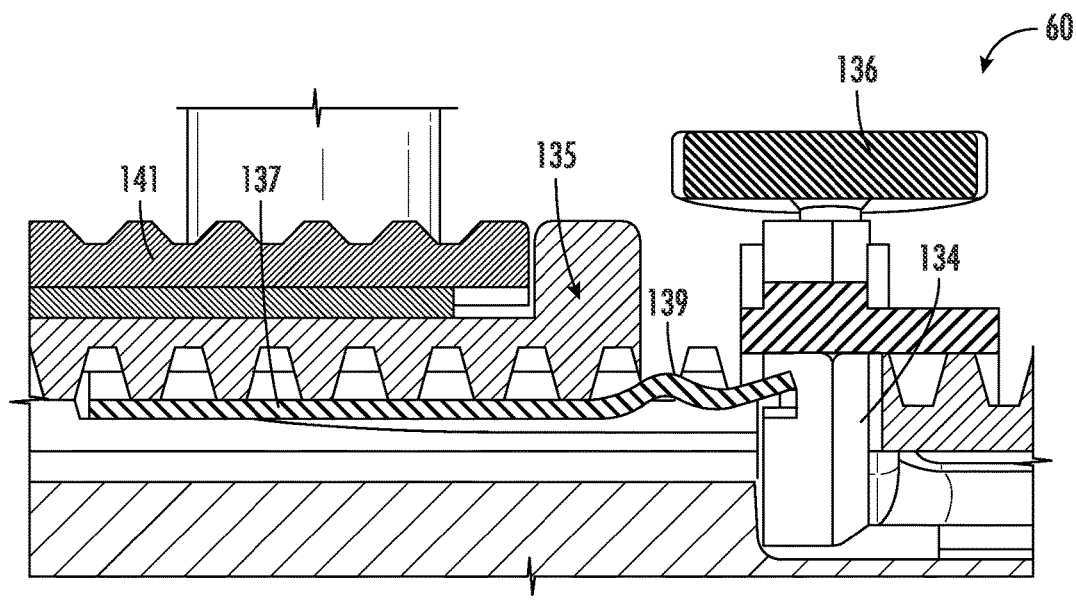
FIG. 15
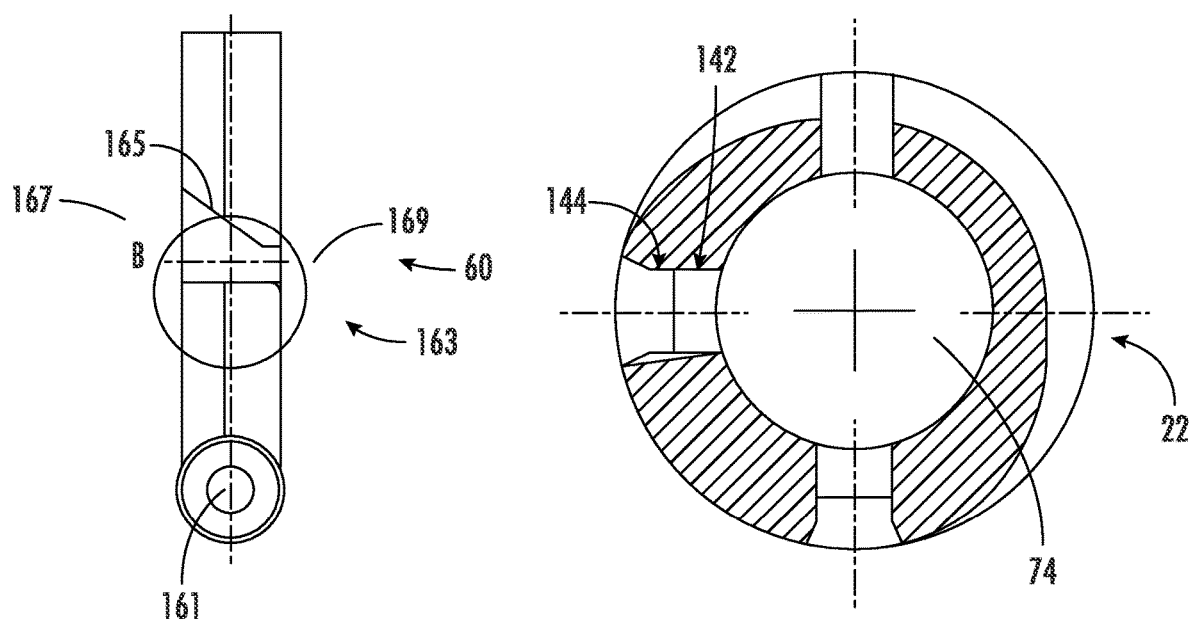
FIG. 16
FIG. 17

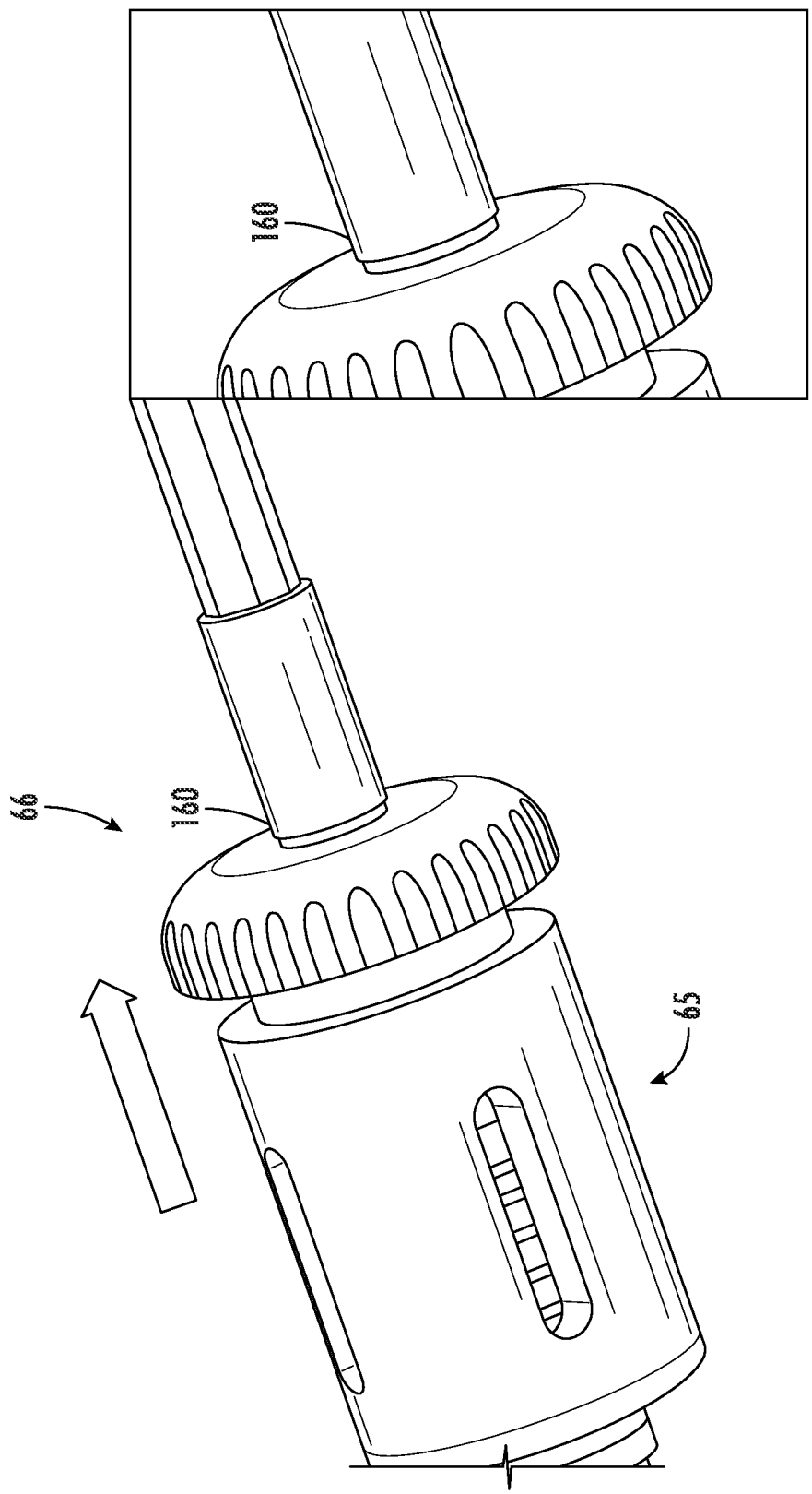

GUIDED SYSTEMS AND METHODS FOR IMPLANTING FASTENERS INTO TISSUE

BACKGROUND

Medical implants have been used in the field of spine, orthopedics and dentistry for over a century, including trauma, fracture repair, reconstructive surgery and repairing or replacing damaged bone. These implants are typically used to replace a missing biological structure, support a damaged biological structure and/or to enhance an existing biological structure.

One example of such medical implants are spinal implants. The integrity of the spine, including its subcomponents such as the vertebral bodies and intervertebral discs that are well known structural body parts forming the spine, are key to a patient's health. These parts may become injured by disease (e.g., by tumor, auto-immune disease and the like) or as a result of wear over time or degeneration caused by the normal aging process, or they may become crushed or damaged as a result of trauma or injury.

Spinal osteosynthesis or arthrodesis, is the fusion of vertebra over a joint space by placing bone graft and/or bone graft substitute to bridge the vertebrae so that new bone grows into the spaces. Arthrodesis immobilizes the joints at the level of the fusion to treat pain caused by the motion or instability of the spine, to avoid the risk of paralytic complications associated with a vertebral fracture or to treat a degenerative or tumor pathology of the spine.

In fusion procedures, pedicle screws are sometimes used as an adjunct to the spinal fusion procedure, serving as a means for gripping a spinal segment or vertebrae. The pedicle screws may be implanted into two or three consecutive spine segments (e.g., L4 and L5) and connected to a rod. The pedicle screws act as firm anchors to hold the rod in abutment against the vertebral bodies. The rod is trapped between the vertebra and the pedicle screws to hold the vertebrae in position during osteosynthesis of the bone.

While these spinal fusion procedures generally provide effective results, they suffer from a number of drawbacks. For example, to achieve high levels of mechanical integrity in the fusion system, and to balance the forces created in the bone structure, it is necessary to advance the pedicle screws into the correct location and at the correct angle (i.e., the screwing axis). This requires extreme precision from the surgeon during the procedure. Vertebrae, like most bone structures, have complex shapes including non-planar curved surfaces making accurate and perpendicular drilling difficult. Moreover, the desired screwing axis may be shifted during drilling, resulting in a screw that is drilled into the wrong position of the bone, or into surrounding tissue and nerves, resulting in severe complications for the patient.

To facilitate the accurate implantation of screws into bone and other tissue, robot-assisted support arms have been created to fix the position of the screwdriver as the screw is tightened within the bone. These support arms more accurately depict the position of the screwdriver in relation to the structures of the patient, and may, for example, aid in eliminating hand tremor and provide the surgeon with an improved ability to work through a small opening in the patients.

Unfortunately, these robot-assisted support arms are expensive, obtrusive and require a cumbersome setup for the robot in relation to the patient and the surgeon. In addition, autonomous movement and precise placement of a surgical instrument can be hindered by a lack of mechanical feedback and/or a loss of visual placement once the instrument has penetrated the outer skin surface of the patient. These drawbacks make the existing surgical applications expensive, burdensome and sometimes error prone, resulting in potential complications in the procedure and safety hazards to the patient.

Accordingly, it would be desirable to provide systems and methods for more accurately advancing fasteners, such as screws, into tissue. It would be particularly desirable to provide systems that maintain the desired screwing axis of the screw, while minimizing the risk of damage to surrounding tissue and nerves.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

Systems, devices and methods are provided for implanting screws into tissue, such as bone. These systems and methods are particularly useful for implanting cannulated screws, such as pedicle screws, into vertebral bodies.

In one aspect, a device for advancing a screw into tissue comprises a screwdriver having a central shaft with a longitudinal axis and a distal end configured for attachment to a screw and an inner lumen for receiving a guidewire. The device further includes a retaining device for holding the guidewire fixed relative to the screw as the screw is advanced in a distal direction and a release device for releasing the guidewire from the screw and holding the guidewire fixed relative to the longitudinal axis as the screw is advanced in the distal direction. This allows a physician to advance a guidewire in front of (i.e., distal to) the screw to more accurately follow a desired screwing axis, and to minimize trauma during tightening of the screw into the tissue. In addition, the guidewire can be released from the screw during implantation such that the guidewire no longer advances with the screw, thereby limiting the distal movement of the guidewire and minimizing damage to surrounding tissue and nerves.

The release device may be configured to allow the guidewire to advance with the screw a fixed distance ("Y") in the distal direction. Once the guidewire has advanced this fixed distance Y, the guidewire stops advancing and is "covered" by the screw. The system may include a visual indicator of this fixed distance Y to allow the physician to set this fixed distance. This allows the physician to determine the precise distance that the guidewire will travel within the target region of the patient before it stops advancing and is covered by the screw.

In embodiments, the retaining device is movably coupled to an outer surface of the central shaft of the screwdriver and comprises a first locking element for fixing a position of the guidewire within the central shaft of the screwdriver. In an exemplary embodiment, the first locking element comprises a pin or screw extending into the inner lumen of the central shaft and configured to engage the guidewire. The retaining member further comprises a rotatable knob coupled to the pin such that rotation of the knob moves the pin inwardly towards the inner lumen of the central shaft.

The central shaft comprises a second locking element for fixing a longitudinal position of the retaining device relative to the central shaft, thereby at least temporarily securing the guidewire to the screwdriver and the screw. In an exemplary embodiment, the central shaft comprises a longitudinal groove and the retaining device comprises an inner pin or shaft extending into, and configured to move through, the longitudinal groove. The central shaft further includes a lateral groove connected to the longitudinal groove. The pin of the retaining device is configured to move through the lateral groove to rotate the retaining device relative to the central shaft. A spring tab on the central shaft is biased such that the retaining device becomes locked within the lateral groove, thereby preventing further longitudinal movement of the retaining device relative to the screwdriver.

The release device may comprise a release member for releasing the second locking element and allowing the retaining device to move in a longitudinal direction relative to the central shaft. This releases the guide retaining device and the guidewire from the screwdriver and screw, allowing the screw to cover the guidewire as it is advanced further distally. In an exemplary embodiment, the release member comprises an inner thread on the proximal end of a support barrel assembly. The inner thread is configured such that, as the retaining device advances distally and engages the support barrel assembly, the inner thread presses downward on the spring tab to thereby release the retaining device. This allows the retaining device to move along the central groove of the shaft such that the retaining device remains fixed in position relative to the support barrel assembly as the screwdriver is advanced in the distal direction.

In embodiments, the longitudinal groove of the central shaft comprises an inner portion and an outer portion. The inner portion has side surfaces that are substantially parallel to each other and the outer portion has side surfaces that extend away from each other in a lateral direction relative to the central shaft. Thus, the side surfaces of the outer portion form an angle with the side surfaces of the inner portion, preferably about 5 degrees to about 20 degrees, and more preferably about 10 degrees. This design minimizes friction between the retaining device and the central shaft as the retaining device is moved along the longitudinal groove.

In another aspect, the system further comprises a screwing barrel assembly configured for coupling to a robotic or mechanical support arm. The screwing barrel assembly includes an internal lumen for receiving the central shaft of the screwdriver to thereby fix a position and angle of the screwdriver relative to the target site on the patient. In embodiments, the screwdriver has an outer thread and the screwing barrel has an inner thread for rotatably engaging the outer thread of the central shaft.

In an exemplary embodiment, at least a portion of the outer thread of the central shaft is flattened to limit contact between the inner threads of the support barrel and the outer threads of the central shaft as the screwdriver is rotated relative to the screw barrel. This minimizes contact between these inner and outer threads and inhibits abrasion or wearing of the inner threads of the screw barrel.

The retaining device preferably has an outer diameter larger than a diameter of the screwing barrel. Thus, as the screwdriver and retaining device move distally during tightening of the screw, the retaining device will engage the screwing barrel, which prevents further movement of the retaining device in the distal direction.

In embodiments, the screwing barrel includes an insert that includes the internal threads. The proximal internal thread on the insert is configured to engage the spring tab on the central shaft of the screwdriver. Engaging the spring tab releases the retaining device from the screwdriver, thereby allowing the screwdriver to continue to advance distally, while the retaining device remains fixed in position. Since the guidewire is secured to the retaining device and the screw is secured to the screwdriver, this causes the screw to advance distally and cover the guidewire, which remains in place.

In another aspect, a system for advancing a screw into tissue comprises a screwdriver, a support barrel, a support arm, a retaining device and a release device. The screwdriver includes a central shaft with a longitudinal axis, an outer thread, a distal end configured for attachment to a screw and an inner lumen for receiving a guidewire. The support barrel has an inner thread for rotatably engaging the outer thread of the screwdriver and an attachment element for coupling to the support arm to fix the support barrel in position relative to a patient. The retaining device is configured to hold the guidewire fixed relative to the screw as the screw is advanced in a distal direction and the release device is configured to release the guidewire from the screw and hold the guidewire fixed relative to the longitudinal axis as the screw is advanced in the distal direction.

In embodiments, the retaining device comprises an annular ring coupled to an outer surface of the central shaft and movable in a longitudinal direction relative to the central shaft. The retaining device further comprises a retention member for securing the guidewire to the retaining device such that the guidewire moves in a longitudinal direction with the retaining device. The central shaft includes a retainer for fixing the retaining device relative to the central shaft, holding the guidewire fixed relative to the screw as the screw is advanced in a distal direction.

In embodiments, the support barrel has a proximal internal thread configured to engage the retaining device and release the retaining device from the central shaft. The support barrier has a larger outer diameter than the retaining device to prevent further distal movement of the retaining device. The release device is configured to allow the guidewire to advance with the screw a fixed distance Y in the distal direction. The system may comprise a visual indicator of this fixed distance Y.

In another aspect, a method for advancing a screw into tissue comprises advancing a guidewire through an internal lumen in a screw, fixing the guidewire relative to the screw, advancing the screw and the guidewire into the tissue and releasing the guidewire from the screw such that the guidewire remains fixed in position as the screw is advanced.

In embodiments, the distal tip of the guidewire is advanced distally of a distal tip of the screw. A distal end of a screwdriver is attached to a head of the screw and rotated to advance the screw into the tissue. The guidewire is secured to the screwdriver such that the screw and the guidewire are advanced together.

In embodiments, a fixed distance Y is set that determines the distance that the guidewire will advance with the screw. The guidewire is released or decoupled from the screw driver when the guidewire has advanced the fixed distance Y.

BRIEF DESCRIPTION OF THE DRAWINGS

The accompanying drawings, which are incorporated in and constitute a part of this description, illustrate several embodiments and together with the description, serve to explain the principles of the devices and methods disclosed herein.

FIG. 15 is a close-up view of the portion of the central shaft shown in FIG. 14;

FIG. 16 is a cross-sectional view of one portion of the retainer device;

FIG. 17 is a cross-sectional view of the inner lumen of the screwdriver;

FIG. 26 is side view of a proximal head for coupling and decoupling the screwdriver to the screw.

DETAILED DESCRIPTION

Particular embodiments are described hereinbelow with reference to the accompanying drawings; however, it is to be understood that the disclosed embodiments are merely exemplary and that the devices and methods disclosed herein may be embodied in various forms. Therefore, specific structural and functional details disclosed herein are not to be interpreted as limiting, but merely as a basis for the claims and as a representative basis for teaching one skilled in the art to variously employ virtually any appropriately detailed structure. Well-known functions or constructions are not described in detail to avoid obscuring the description in any unnecessary detail. It should be understood also that the drawings are not drawn to scale and are not intended to represent absolute dimensions or relative size. Instead, the drawings help to illustrate the concepts described herein.

Systems and devices are provided for implanting screws into tissue. The systems and devices are particularly useful for implanting screws into bone tissue, such as pedicle screws in vertebral bodies. In certain aspects, the systems and devices are advantageous in the field of spinal osteosynthesis for implanting pedicle screws, while maintaining the desired screwing axis of the screw and minimizing the risk of damage to surrounding tissue and nerves.

While the following is presented with respect to a system for implanting a pedicle screw into vertebrae, it should be understood that certain features of the presently described devices may be readily adapted for use in advancing and/or implanting any type of surgical instrument into tissue in a patient. For example, the systems described herein may be used for advancing fasteners into bone plates for compression of a fracture site or osteotomy of a bone, artificial joints, such as hip or knee replacements, artificial discs, interbody fusion devices (e.g., cages) and the like.

Figure 1:
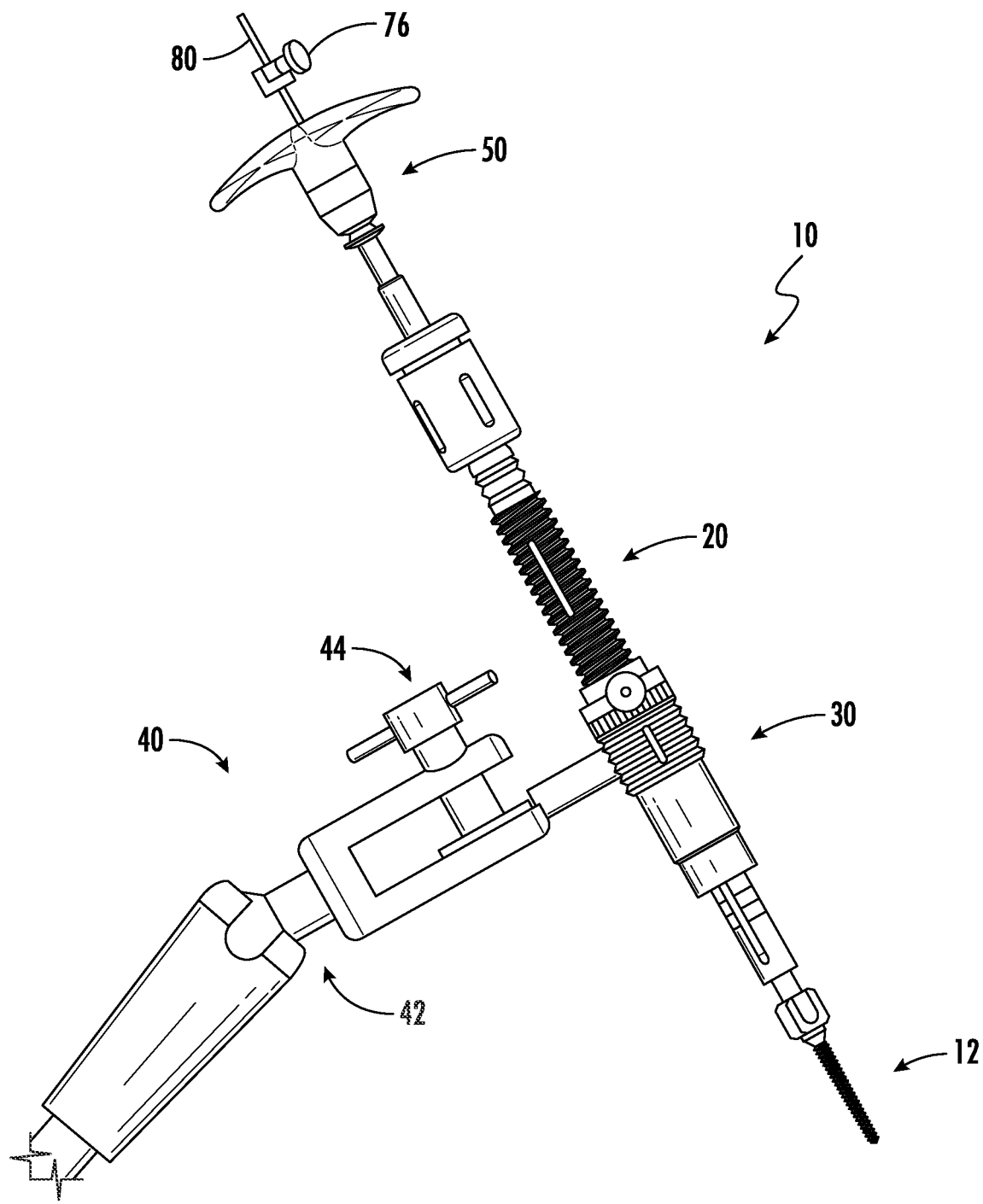
FIG. 1 is a perspective view of a system for implanting a cannulated screw.

Referring now to FIG. 1, a system 10 for implanting a screw 12 into tissue, such as bone tissue, will now be described. System 10 comprises a screwdriver 20, a support barrel assembly 30 and a support arm 40. In some embodiments, screw 12 may be a cannulated pedicle screw having an internal lumen for receiving a guidewire 80.

The support arm 40 comprises an articulable member or members 42 and a locking member 44 that couples support arm 40 to barrel assembly 30 and functions to fix a position of support barrel assembly 30 to a reference point related to the patient's tissue, e.g., the target site within the vertebrae. This reference point can, for example, be linked, directly or indirectly, to the operating table or any other structure in the operating room. Of course, the screwdriver 20 described herein may be used with a variety of different support arms or other systems for fixing a position and angle of the screwdriver that are known to those of skill in the art. A more complete description of one such suitable support arm can be found in French Patent No. 3106483, the complete disclosure of which is incorporated herein by reference in its entirety for all purposes.

Support arm 40 (or other known support arms) may be manually articulated by the physician, or it may be controlled by a suitable robotic control system. Suitable robotic control systems for use with the implantation system disclosed herein can be found in U.S. Pat. Nos. 8,010,181, 9,782,229, 9,078,685, 10,357,184, 10,646,280, 10,638,112, 11,103,320, 11,109,922, 10,799,298 and US Publication No. 2018/0147108, the complete disclosures of which are incorporated herein by reference in their entirely for all purposes.

Figure 2A:
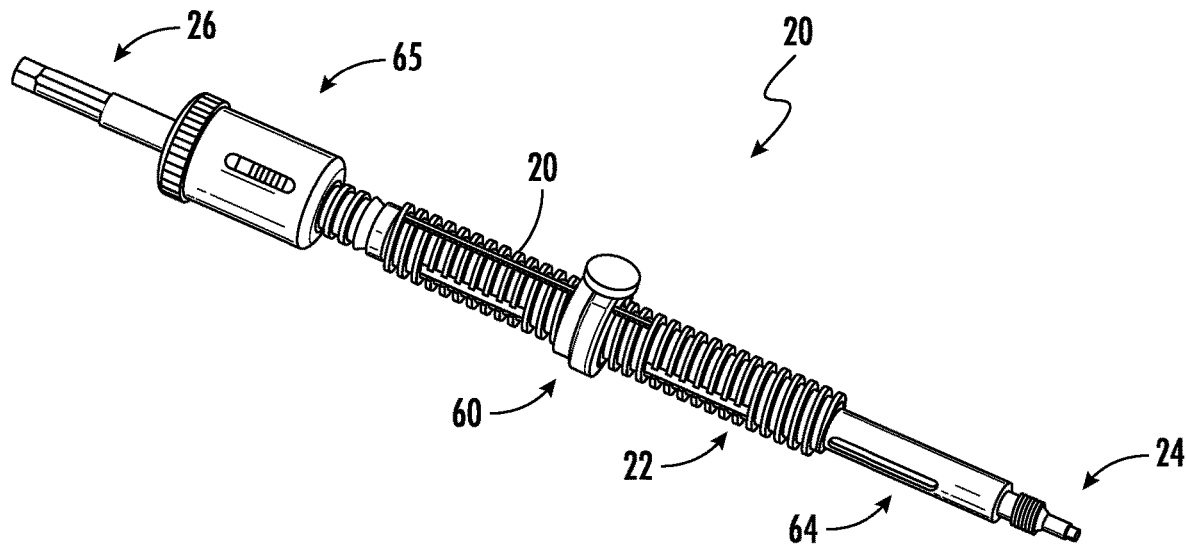
FIG. 2A is a perspective views of a screwdriver of the system of FIG. 1.
Figure 2B:
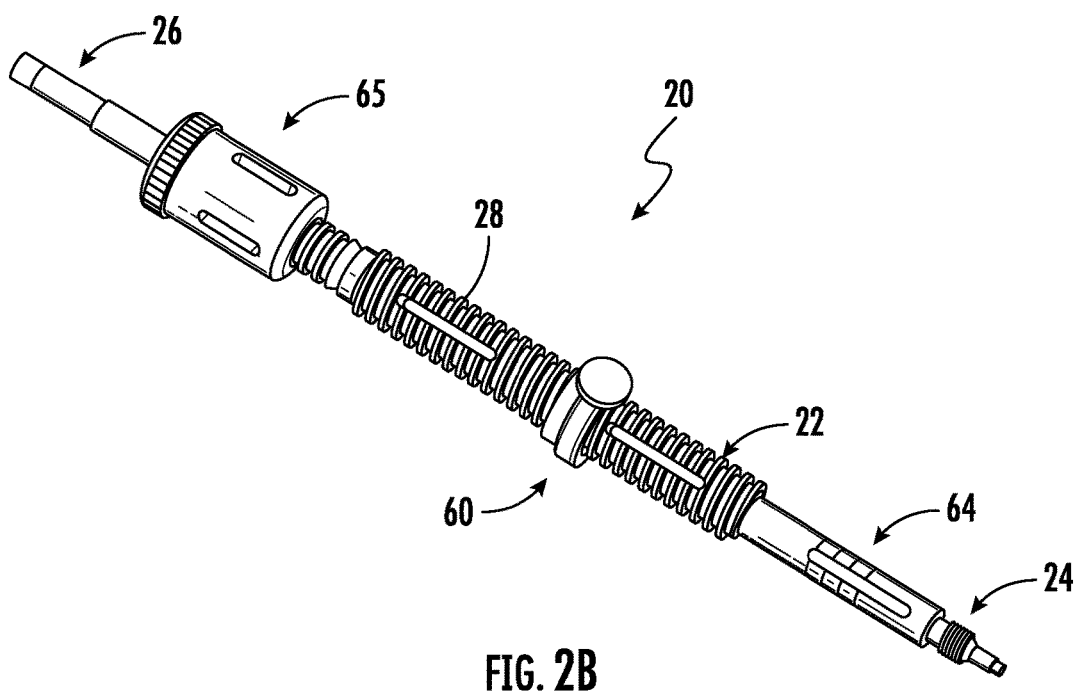
FIG. 2B is a perspective view of the screwdriver of FIG. 2A in a different orientation.
Figure 3:
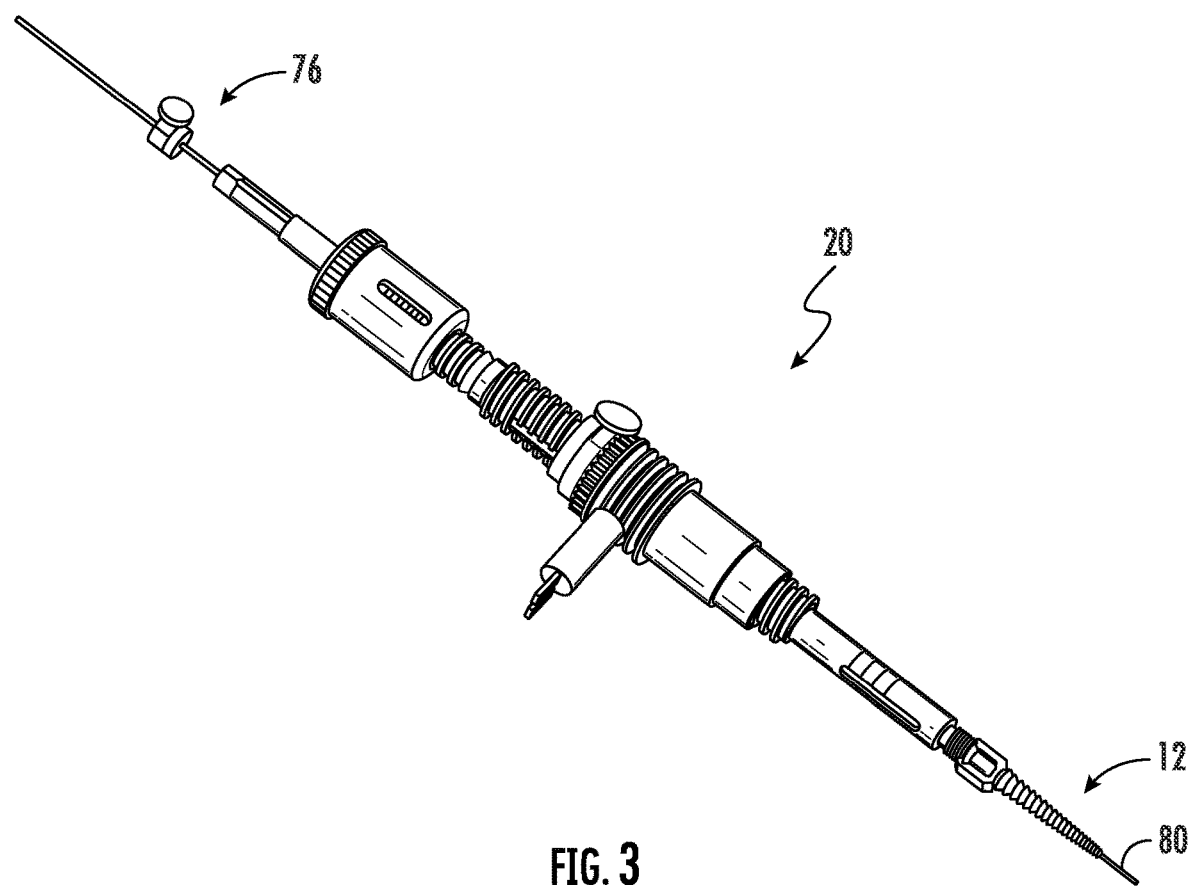
FIG. 3 illustrates the screwdriver of FIGS. 2A and 2B coupled to a screw and a guidewire.

Referring now to FIGS. 2A, 2B and 3, screwdriver 20 comprises a central shaft 22 with a distal end 24 configured for coupling to screw 12 and a proximal end 26 configured for coupling to a handle 50 (see FIG. 1). Central shaft 22 includes an outer threaded portion 28 that is configured for engaging an inner threaded portion 141 of support barrel assembly 30 (see FIG. 15). Rotation of screwdriver 20 relative to support barrel assembly 30 causes screwdriver 20 to move in the longitudinal direction relative to support barrel assembly 30. Support barrel assembly 30 maintains the screwing axis of screwdriver 20 as it is advanced towards the target site of the patient.

In certain embodiments, the threads of outer threaded portion 28 and the inner threaded portion 141 of support barrel assembly 30 have substantially the same pitch Pa as the thread of screw 12. In other embodiments, outer threaded portion 28 and/or inner threaded portion 141 have a different pitch as the thread of screw 12.

Screwdriver 20 further includes a retaining device 60 mounted to an outer surface of central shaft 22 and movable relative to the shaft 22 in the longitudinal direction. In one embodiment, retaining device 60 moves or slides longitudinally relative to shaft 22 along a central groove 62 within shaft 22 (see, for example FIG. 9). Screwdriver 20 further includes a visual indicator 64 of a distance Y near the distal end of central shaft 22 and a proximal head 65 for facilitating the release of screw 12 from screwdriver 20 (discussed in more detail below).

Figure 12:
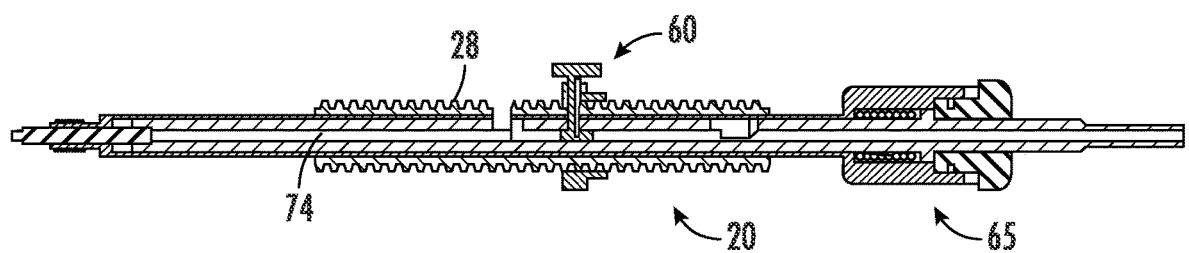
FIG. 12 is a cross-sectional view of the screwdriver, illustrating an inner lumen for receiving the guidewire.
Figure 13A:
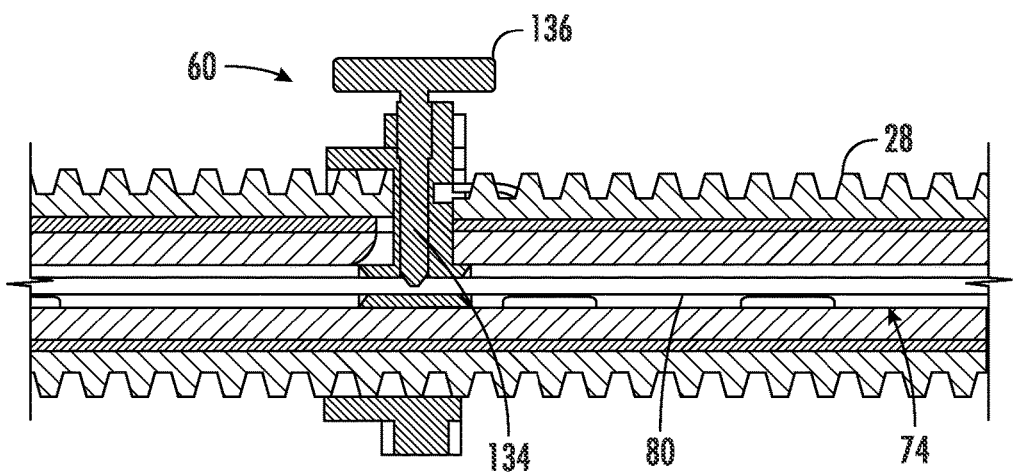
FIG. 13A is an enlarged cross-sectional view of a portion of the screwdriver, illustrating the retaining device securing the guidewire within the inner lumen of the screwdriver.
Figure 13B:
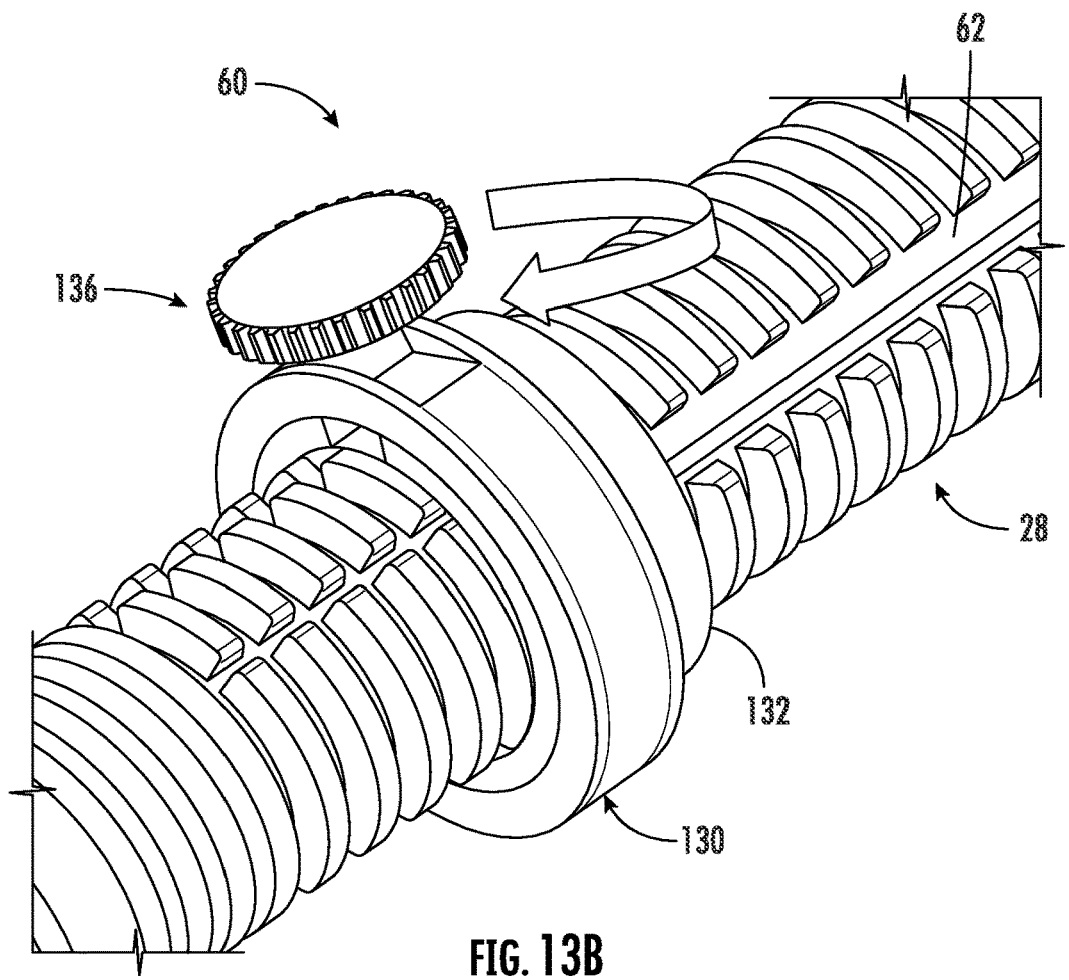
FIG. 13B is an enlarged perspective view of a rotatable knob on the retaining device.

As shown in FIGS. 3 and 12, screwdriver 20 further includes an internal lumen 74 for receiving a guidewire 80 therethrough, and a guidewire indicator 76 on a proximal portion of screwdriver 20 for indicating a position of the guidewire 80 relative to the screw 12 (discussed in more detail below). Guidewire 80 may be any suitable guidewire used by those skilled in art, such as a Kirschner wire or K-wire, a solid core wire, mandrel wire, ribbon wire, or the like.

Figure 4:
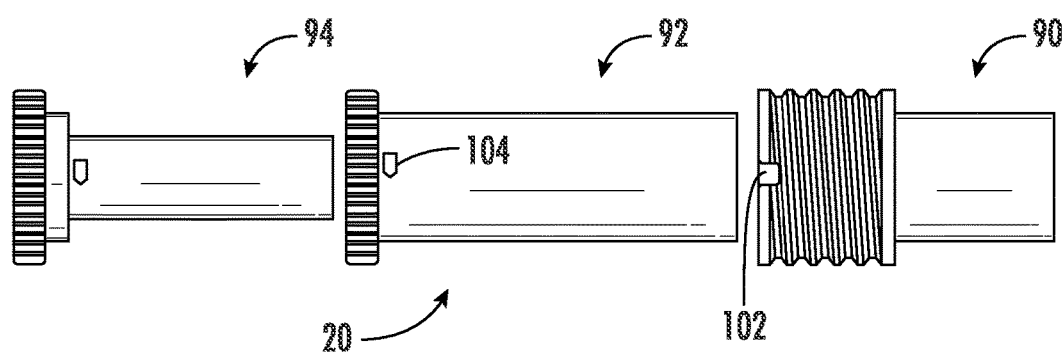
FIG. 4 is an exploded view of components of a support barrel assembly for use with the screwdriver.
Figure 5:
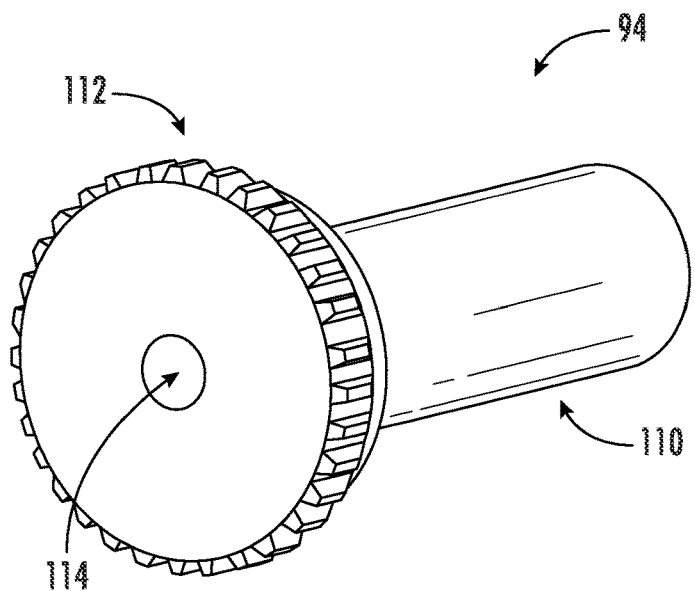
FIG. 5 is a perspective view of a reducer component of the support barrel assembly of FIG. 4.
Figure 6:
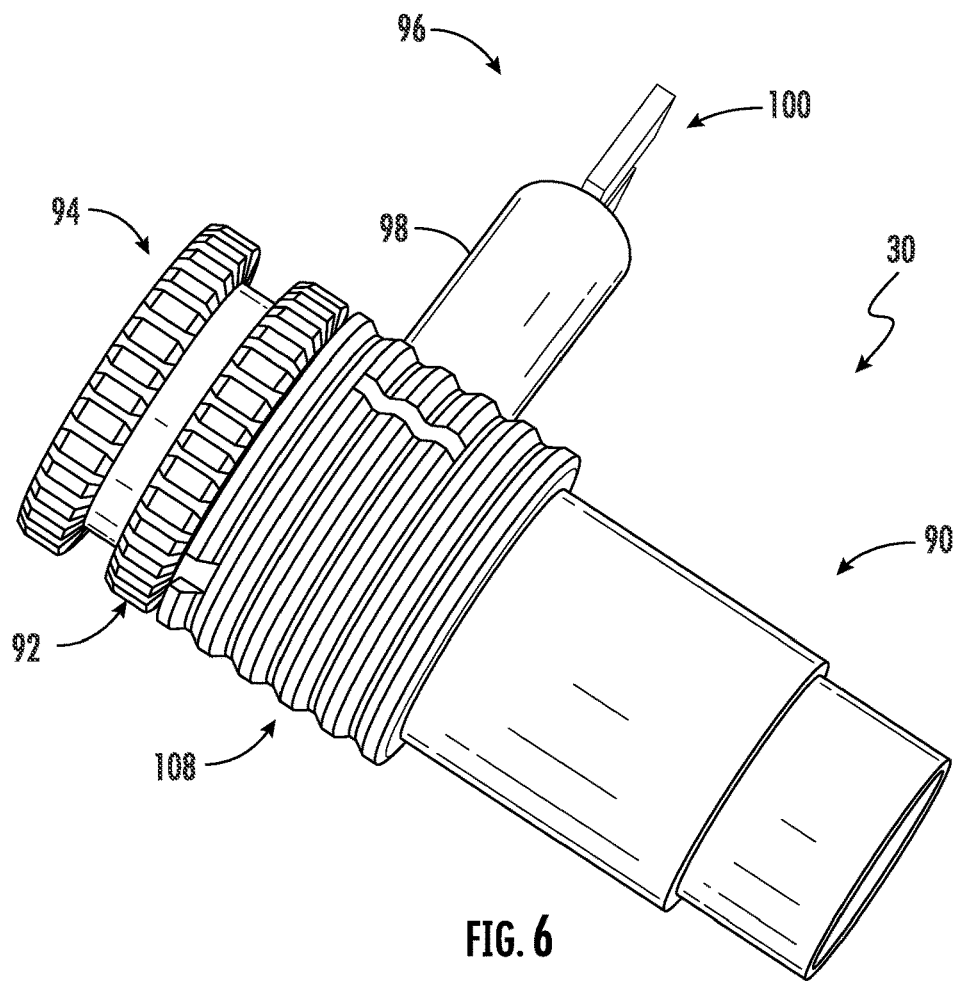
FIG. 6 is a perspective view of an assembled support barrel.

Referring now to FIGS. 4-6, support barrel assembly 30 comprises a screw barrel 90, an insert 92 and a reducer 94. Insert 92 comprises inner threads 141 (see FIG. 15) configured to engage outer threaded portion 28 of screw driver 20 such that screwdriver 20 can be rotated within screw barrel assembly 30 to advance screw 12 into tissue while screw barrel assembly 30 remains substantially fixed in position (as screw barrel 90 is mounted to support arm 40). Screw barrel 90 comprises an attachment member 96 for mounting barrel 90 to support arm 40. In one embodiment, attachment member 96 includes an elongate member 98 extending from barrel 90 and a forked attachment element 100 that mounts to the support arm 40. Screw barrel 90 furthers includes a gripping portion 108 on a proximal portion of barrel 90 to facilitate gripping of barrel 90 during assembly of support barrel assembly 30.

Figure 7A:
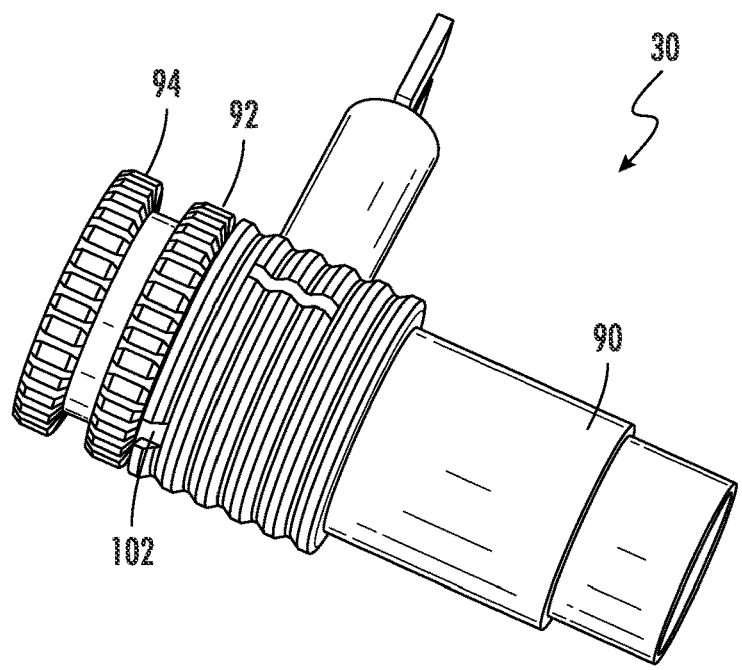
FIGS. 7A-7C illustrate the steps to assemble the components of the support barrel assembly.
Figure 7B:
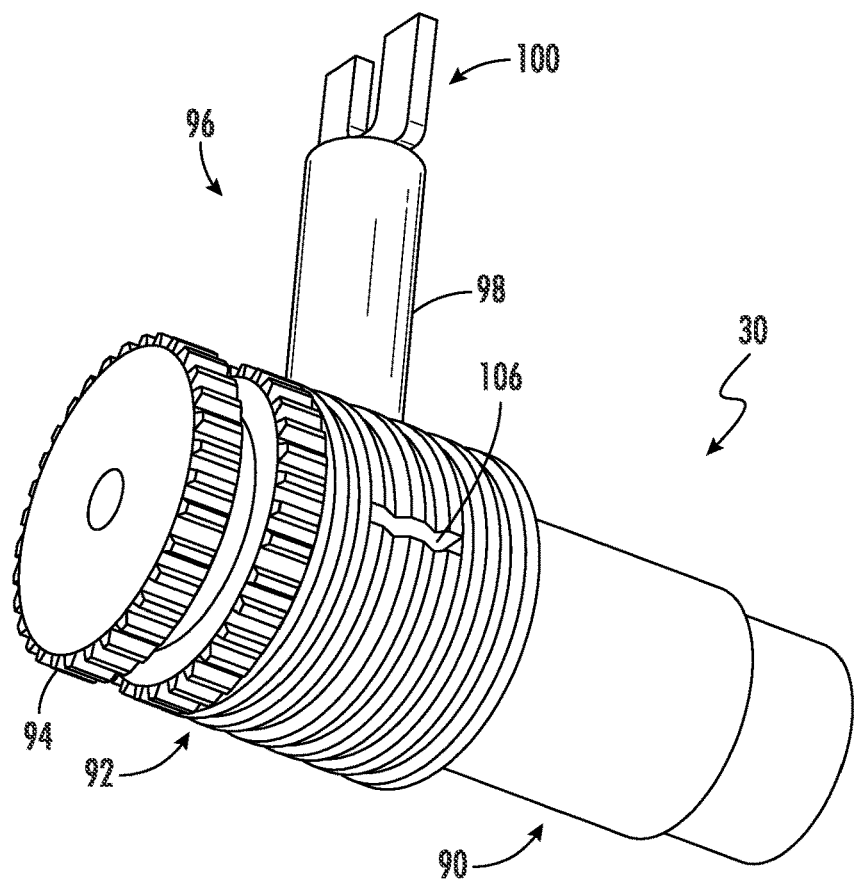
Figure 7C:
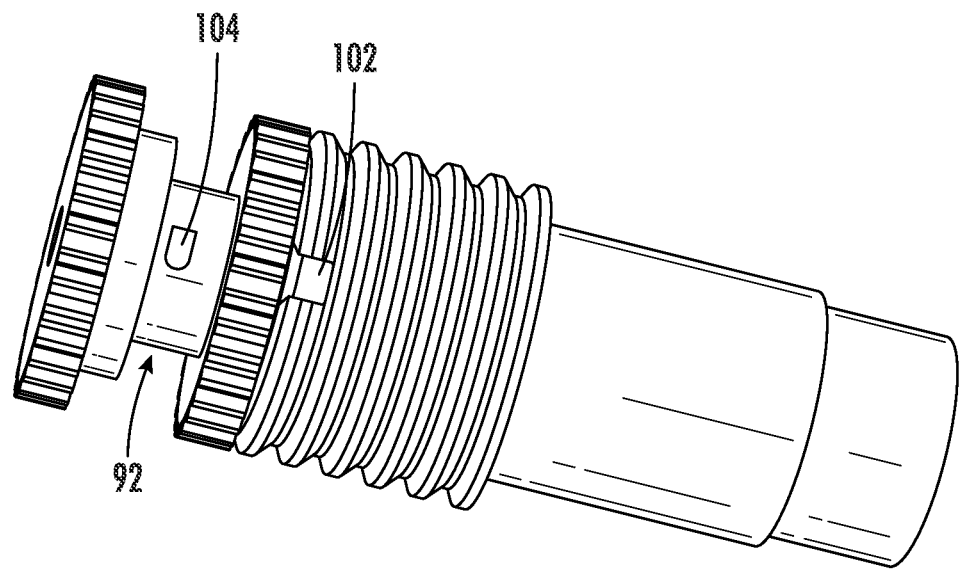

Referring now to FIGS. 7A-7C, screw barrel 90 further includes a notch 102 for receiving a protrusion 104 on insert 92. Insert 92 can be quickly and easily inserted into screw barrel 90 and rotated until protrusion 104 slides within notch 102 to couple insert 92 to screw barrel 90. Screw barrel 90 further includes a lug 106 that ensures that the insert 92 remains locked to barrel 90.

As shown in FIG. 5, reducer 94 comprises a central shaft 110 coupled to a proximal member 112 having a central hole or opening 114. Central hole 114 is preferably sized to receive an elongate member having a smaller diameter than barrel 90, such as a pointer or other equivalent device, for fixing an orientation or angle of screw system 10 (i.e., the screwing axis) relative to the target site on the patient. In an exemplary embodiment, hole 114 has a diameter of about 6 mm.

As shown in FIGS. 7A-7C, reducer 96 can be screwed into insert 94 by rotating it relative to insert 94, e.g., a quarter turn. Once reducer 96 has been attached to insert 94, the pointer is inserted through hole 114. Screw barrel 90 is then unlocked from support arm 40 so that the barrel 90 can be rotated to the desired orientation (based on the pointer that passes through hole 114 and is advanced to the target site on the patient). Once the proper orientation for the screwing axis has been achieved, barrel 90 can be locked back onto support arm 40 and the pointer is removed. Reducer 96 may then be rotated counterclockwise a quarter turn to remove reducer 96 from insert 94.

Figure 8:
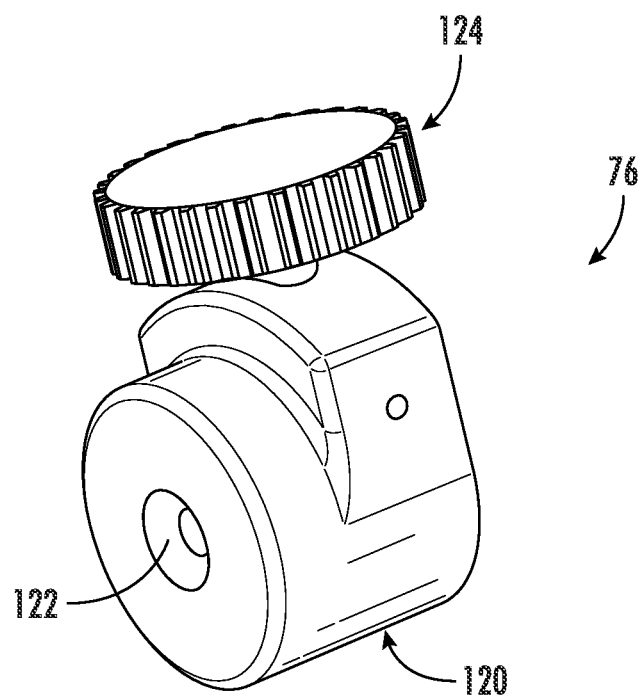
FIG. 8 is a perspective view of a guidewire indicator.

Referring now to FIG. 8, guidewire indicator 76 comprises a central shaft 120 with a lumen 122 for receiving guidewire 80 and an external rotatable knob 124. Rotatable knob 124 is coupled to an internal screw (not shown) for securing guide indicator 76 to guidewire 80. Rotation of knob 124 in one direction (e.g., clockwise) causes internal screw to move inwards to secure indicator 76 to guidewire 80 and rotation in the other direction (e.g., counterclockwise) moves internal screw outwards to release indicator 76 from guidewire 80.

Referring now to FIGS. 9-16, retaining device 60 comprises an annular slide member 130 and an annular retainer ring 132, each having an inner diameter larger than the outer diameter of central shaft 22 so that retaining device 60 may slide along central shaft 22 in the longitudinal direction. To that end, retaining device 60 further includes an elongate pin or screw 134 that extends inwardly into central groove 62 of central shaft 22 and a rotatable knob 136 coupled to screw 124. As shown in FIGS. 13A and 13B, rotation of knob 136 moves screw 134 inward and outward relative to the longitudinal axis of shaft 22 such that retaining device 60 fixes the position of guidewire 80 relative to retaining device 60.

Figure 9:
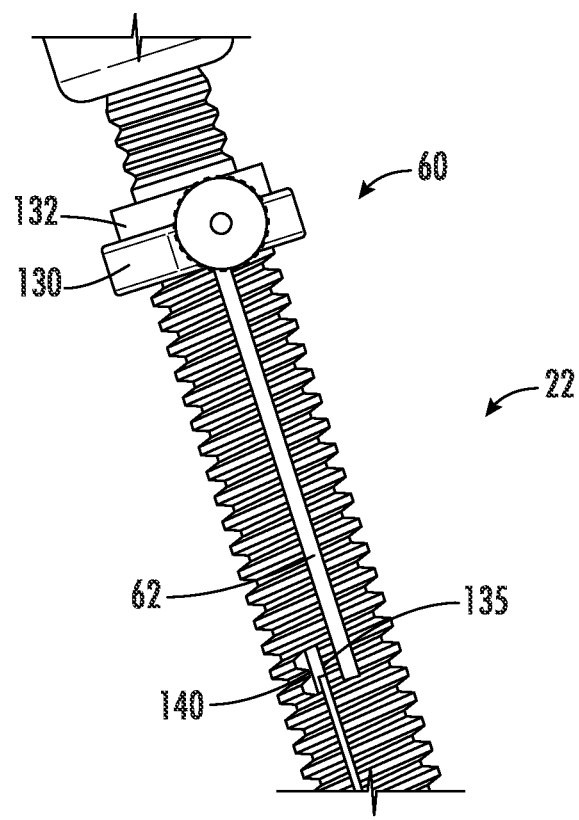
FIG. 9 is a partial view of the screwdriver, illustrating a portion of a central shaft with a retaining device coupled thereto.
Figure 11:
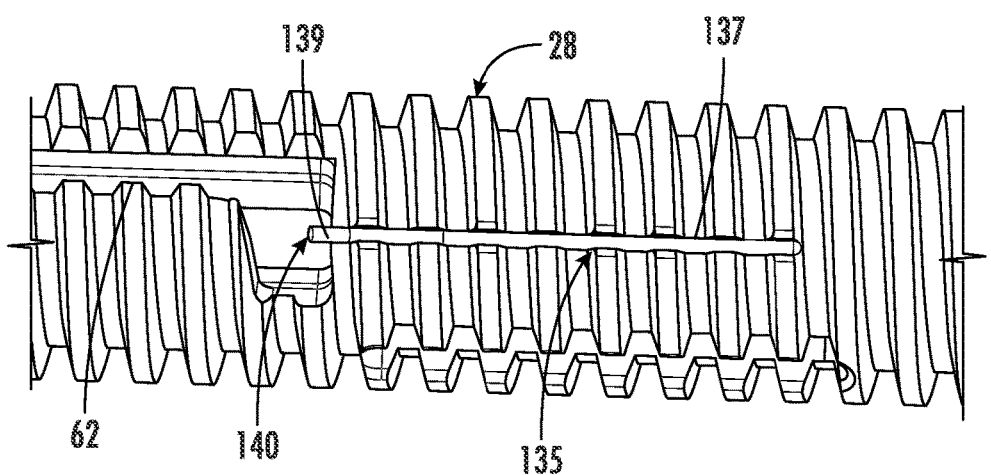
FIG. 11 is a close-up of the lateral groove and a spring tab.

As shown in FIGS. 9 and 11, central shaft 22 further includes a lateral groove 140 at the distal end of central groove 62. Lateral groove 140 extends circumferentially around a portion of central shaft 22 and is designed such that elongate screw 134 of retaining device 60 may be rotated into lateral groove 140 to prevent further movement of retaining device 60 relative to central shaft 22.

Figure 14:
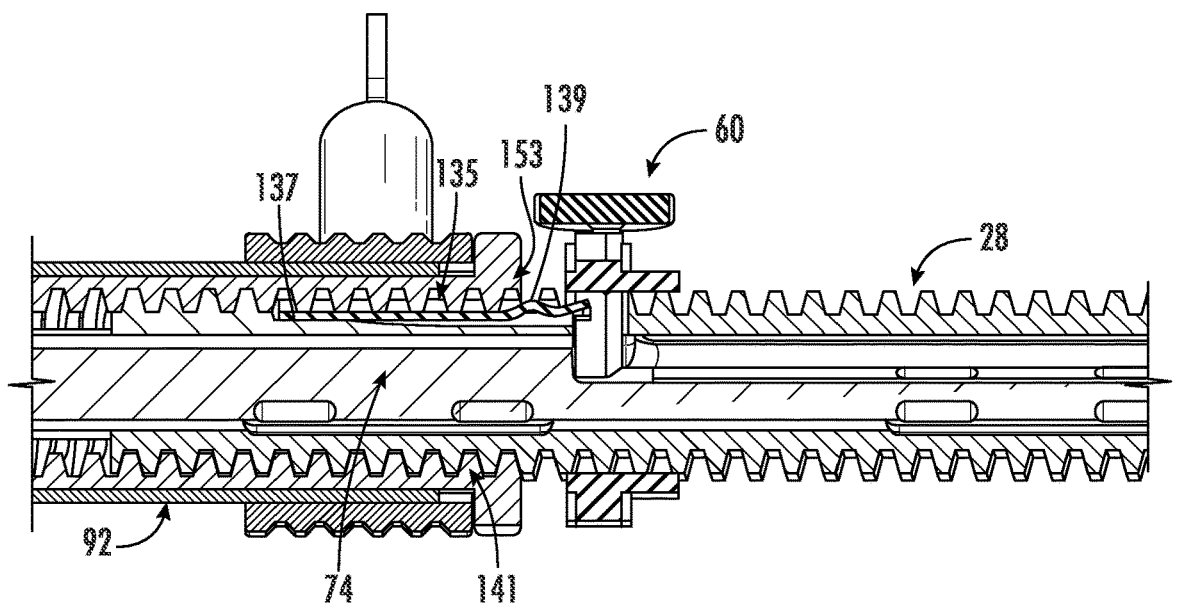
FIG. 14 is a cross-sectional view of a portion of the central shaft of the screwdriver, illustrating a spring tab engaging the retaining device within the lateral groove.

As shown in FIGS. 14-16, central shaft 22 further includes a spring tab 135 that has an elongate portion 137 extending along shaft, and a curved portion 139 extending at least partially into lateral groove 140. Curved portion 139 of spring tab 135 preferably has a curvature that allows the highest point of curved portion 139 to contact inner threads 141 of insert 92. These inner threads 141 engage and contact curved portion 139 of spring tab 135 when screwdriver 20 is rotated distally relative to screw barrel 90 and retaining device 60 moves into contact with, or adjacent to, the proximal portion of insert 92. The proximal inner thread 141 of insert 92 pushes curved portion 139 of spring tab 135 downwards or towards the longitudinal axis of central shaft 22.

Curved portion 139 of spring tab 135 is preferably disposed at, or adjacent to, the last opening 153 in outer threaded portion 28 just distal of lateral groove 140. This allows spring tab 135 to be pushed down at the minimal distance between retaining device 60 and insert 92.

Elongate portion 137 of spring tab 135 is preferably substantially planar or flat so that it does not contact inner threads 141 of insert 92. Elongate portion 137 is disposed underneath outer threaded portion 38 (see FIG. 15), and the spring tab 135 welcoming zone on threaded portion 38 is deeper than the bottom of the thread, so that elongate portion 137 does not contact inner threads 141 of insert 92

Referring now to FIG. 16, retaining device 60 comprises a longitudinal opening 161 for allowing passage of guidewire 80 therethrough. In addition, retaining device 60 includes an internal threaded portion (not shown) configured to engage with an external threaded portion of screw 134 such that rotation of knob 136 causes screw 134 to rotate relative to these internal threads and move inwards and outwards relative to knob 136, thereby allowing screw 134 to engage and secure guidewire 80 in place relative to retaining device 60.

Retaining device 60 further induces a lateral opening 163 that extends from one side of the device 60 to the other. Lateral opening 163 has an inclined surface 165 one side of opening 163 that tapers inwardly towards the center of retaining device 60. This creates a first opening 167 that is larger than a second opening 169. When retaining device 60 is located within central groove 62 (i.e., before it has passed into lateral groove 140), curved portion 139 of spring tab 135 is located adjacent first opening 167 of retaining device 60 (i.e., to the left of opening 167 in FIG. 16). Movement of retaining device 60 through lateral groove 140 causes spring tab 135 to pass through lateral opening 163 from first opening 167 to second opening 169 (i.e., by sliding down inclined surface 165 from left to right in FIG. 16). After retaining device 60 is fully positioning in lateral groove 140, spring tab 135 is located adjacent second opening 169 (i.e., to the right of retaining device 60 in FIG. 16). Curved portion 169 of spring tab 135 is then biased upwards such that it is disposed above second opening 169. This prevents retaining device 60 from moving back to the right and secures retaining device 60 within lateral groove 140.

Spring tab 135 is preferably designed such that the curved portion 169 is biased upward (i.e., outward from the longitudinal axis of central shaft 22). Spring tab 135 may comprise any suitable material, such as a short stainless steel wire. The length and diameter of the wire is selected to provide sufficient flexion on curved portion 139 to allow curved portion 139 to pass through first opening 167 of lateral opening 163 of retaining device 60 and to allow internal threads 141 of insert 92 to press down on spring tab 135 such that it may pass back through second opening 169 of retaining device. In addition, this length and diameter is selected to provide sufficient rigidity to curved portion 139 to maintain its position as shown in FIG. 15 when no force is exerted against curved portion 139. In one exemplary embodiment, the length of elongate portion 137 is about 20 to 40 mm, or about 30 to 35 mm.

Referring now to FIG. 17, in certain embodiments, central groove 62 of shaft 22 includes an inner portion 142 and an outer portion 144. Inner portion 142 comprises side walls that are substantially parallel to each other, extending laterally outward from inner lumen 74. Outer portion 144 includes side walls that extend laterally away from each other to form an angle with the side walls of inner portion 142. The angle may be between about 5 degrees to about 30 degrees, preferably between about 5 degrees and 15 degrees. In an exemplary embodiment, this angle is 10 degrees. This configuration reduces friction between elongate screw 124 and central shaft 22 as retaining device 60 moves through central groove 62.

Figure 18:
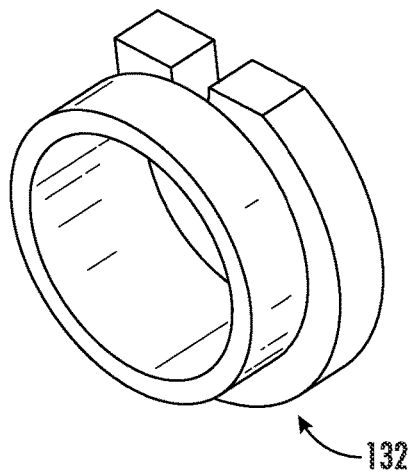
FIG. 18 is a perspective view of an outer ring of the retaining device.

Referring now to FIG. 18, in certain embodiments, retaining device 60 includes a separate outer ring 132 coupled to retaining ring 130. Outer ring 132 preferably comprises a material that inhibits friction with central shaft 22 as retaining device 60 is moved along central groove 62, such as a polymer (e.g., PTFE) or the like.

Figure 19:
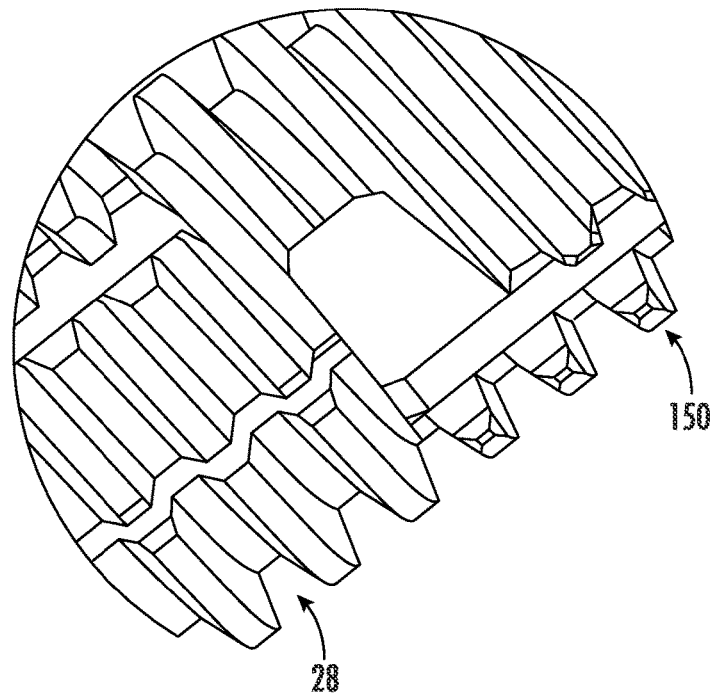
FIG. 19 is a side view of a portion of the outer threads on the screwdriver.

Referring now to FIG. 19, in certain embodiments, at least a portion of outer threaded portion 28 of central shaft 22 includes threads that have been flattened, i.e., having a substantially planar outer surface. As shown, this flattened portion 150 is preferably located in the distal portion of central shaft 22 that engages inner threads 141 of insert 92 to limit or inhibit contact between the outer threaded portion 28 and internal threads 141 of insert 92. In certain embodiments, insert 94 comprises a relatively inexpensive material, such as plastic or the like, that can be disposable and single-use. This plastic material can be torn or abraded by the metal threads of screwdriver 22, resulting in the formation of strips or chips or torn material. Applicant has discovered that by slightly flattening certain threads on the screwdriver 22 solves this problem.

In use, the components of barrel assembly 30 are assembled together as discussed above in reference to FIGS. 7A-7C. The barrel 92 is then mounted to support arm 40 by coupling attachment element 100 to the articulatable arm of support arm 40. The physician may then orient barrel 92 relative to the target site of the patient to establish the desired screwing axis. The angle of orientation or screwing axis may be determined by inserting a pointer or other instrument through reducer 96, as discussed above. The reducer 96 may then be removed from barrel assembly 30 so that it is ready to receive screwdriver 20. The position of support barrel 92 relative to the target site on the patient may be selected at this point, or it may be selected after the physician has determined the distance "Y", as discussed below.

Figure 20:
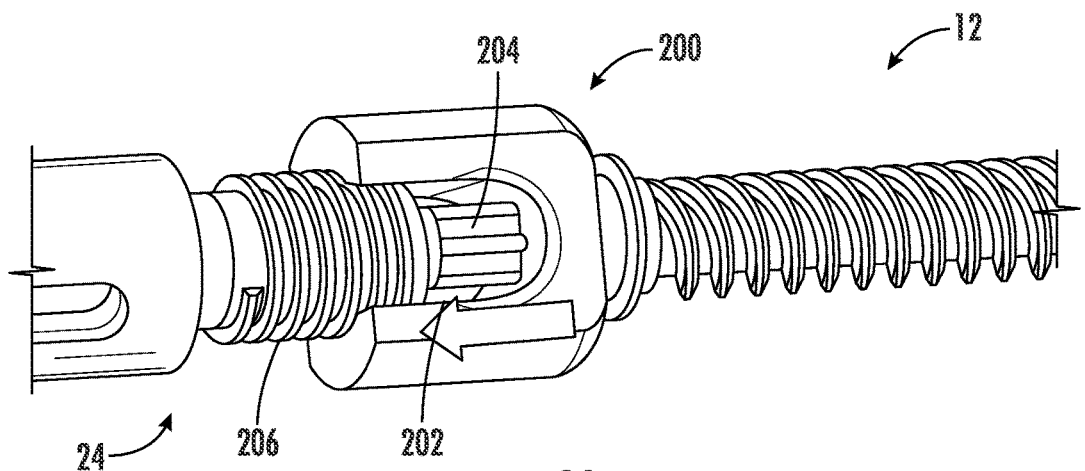
FIG. 20 is a side view of a distal portion of the screwdriver attached to a head of a screw.

As shown in FIG. 20, distal end 24 of screwdriver 20 is attached to screw 12. In certain embodiments, screw 12 is a bone screw, such as a pedicle screw, that may include a recess 202 in a screw head 200, such as a tulip. Screwdriver 20 includes a threaded portion 206 and a mating feature 204, such as a Torx or other similar element. Mating feature 204 engages recess 202 and screw head 200 is rotated to couple the inner threads of screw head 200 to threaded portion 206 of screwdriver 20.

Figure 21:
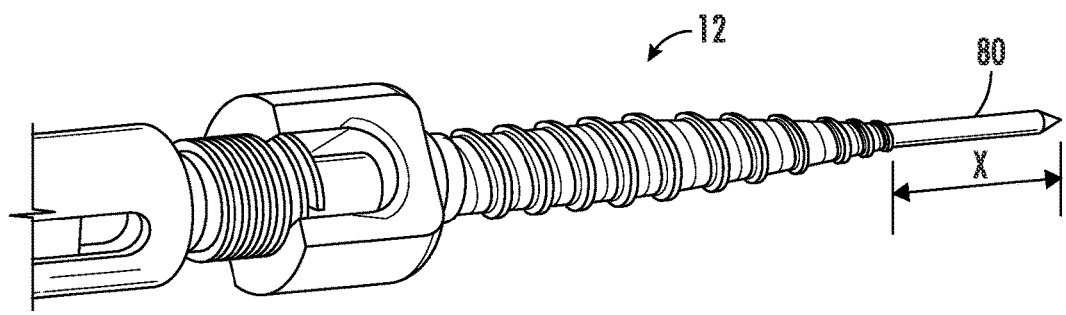
FIG. 21 is a side view of the distal portion of the screwdriver, illustrating a guidewire extending from the distal tip of the screw.
Figure 22:
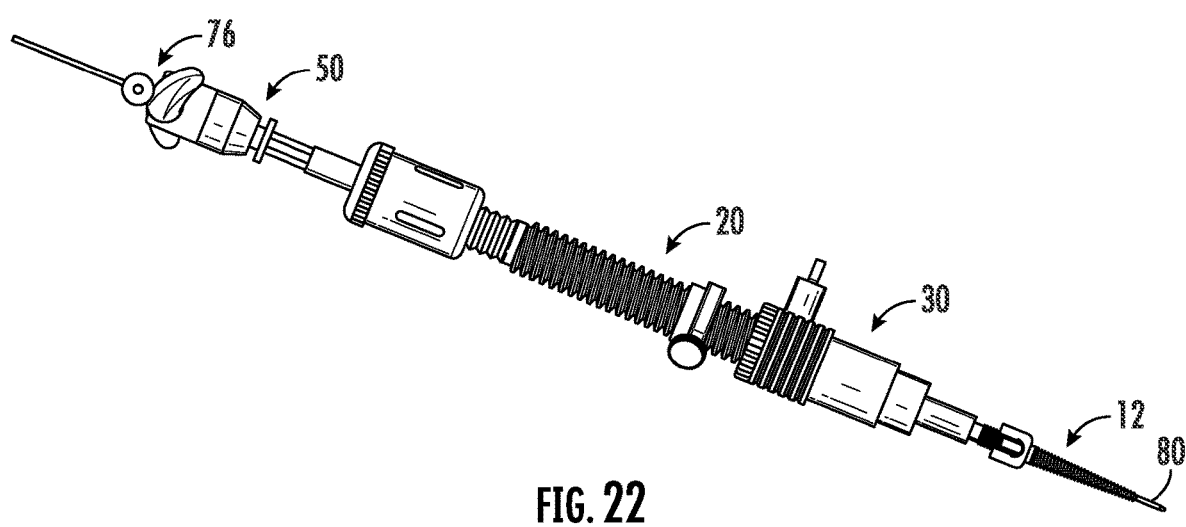
FIG. 22 is a perspective view of the screwdriver attached to the screw and containing a proximal handle for rotating the screwdriver and the screw.

As shown in FIGS. 21 and 22, guidewire 80 is inserted through internal lumen 74 of screwdriver 20 and through the inner lumen of cannulated screw 12. Guidewire 80 may be advanced beyond the distal end of screw 12 to facilitate advancement of screw 12 into the patient's tissue or bone. Guidewire indicator 76 is attached to the proximal end of guidewire 80 such that guidewire indicator 76 is adjacent to or in contact with proximal handle 50 in certain situations (discussed in more detail below).

Figure 10:
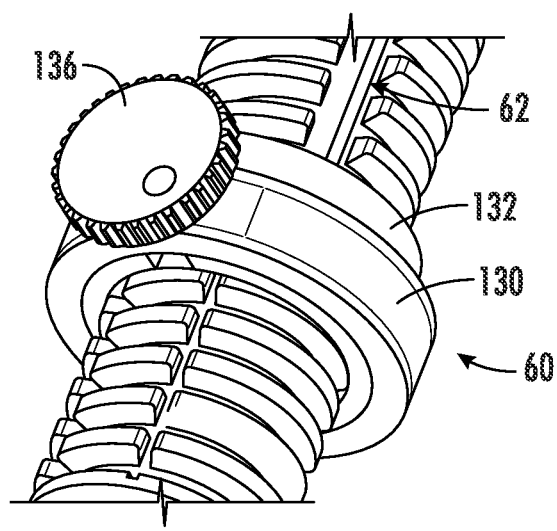
FIG. 10 is a close-up view of the retaining device locked within a lateral groove on the central shaft.

As shown in FIG. 10, retaining device 60 is then locked into position in lateral groove 140 by sliding device 60 to the distal end of central groove 62 and then rotating it through lateral groove 140. Retaining device 60 will be automatically locked into lateral groove 140 by spring tab 135 within central shaft 22, as discussed above.

At this point, the physician may choose to set a distance X that the guidewire 80 will extend distally past the distal end of screw 12 (see FIG. 21). This can be accomplished simply by advancing guidewire 80 through screwdriver 20 and screw 12 until guidewire 80 extends a suitable distance X beyond screw 12.

Once the distance X has been set, rotatable knob 136 of retaining device 60 is rotated to advance internal screw 134 into central shaft 22 and tightened against guidewire 80. This step temporarily locks the position of guidewire 80 relative to the screwdriver 20 and screw 12.

At this point, the surgeon may choose the distance Y (see FIGS. 23A-23D). Y is the distance in which the screw 12 and guidewire 80 will advance before the guidewire 80 stops advancing and begins to retract within screw 12 (i.e., the distance before screw 12 begins to cover the guidewire 80 (see also FIGS. 25A-25C). To do so, the physician determines the distance between retaining device 60 and the target site on the patient. This distance may, for example, be determined by three factors: (1) the length of the screw 12, which is typically about 30 mm to about 65 mm; (2) the length of X, which has been determined by the surgeon in the step above; and (3) the length Y, which is the distance between retaining device 60 and insert 92 after screwdriver 20 has be placed into screw barrel assembly 30.

The distance Y may be selected manually by the physician. Alternatively, the distance Y may be selected with a separate pointer or indicator device that takes into account the length of the screw and the length of X. This pointer allows the surgeon to determine the distance between the retaining device 60 and insert 92. In certain embodiments, the distance Y may be selected by a suitable robotic control system, such as those described above.

Figure 23A:
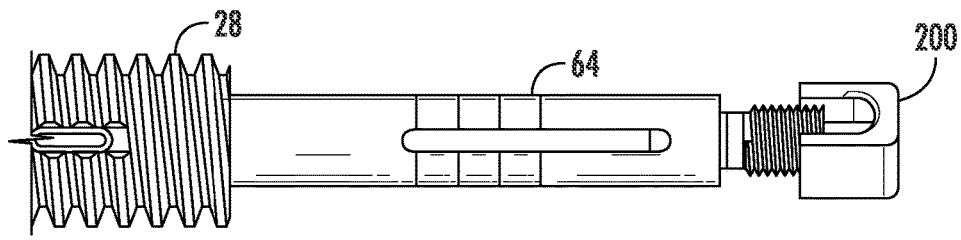
FIGS. 23A-23D illustrate visual markers on the screwdriver corresponding with a distance Y between the retaining device and the screw barrel.
Figure 23B:
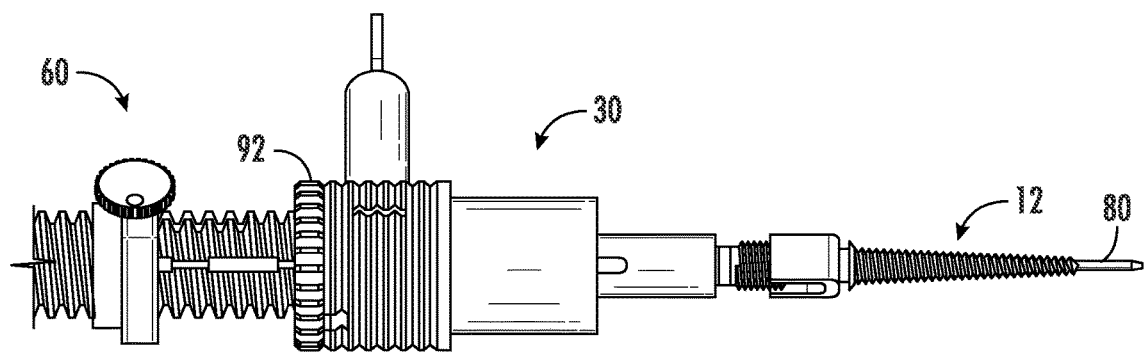
Figure 23C:
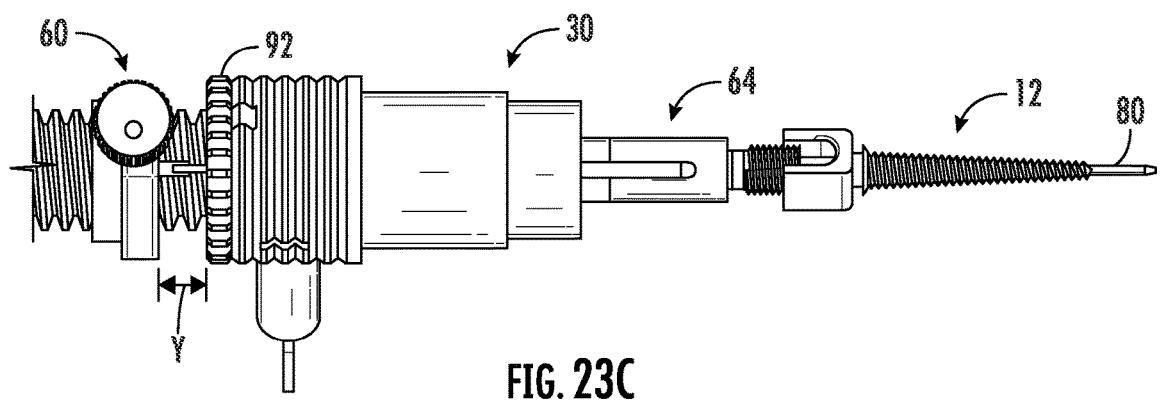
Figure 23D:
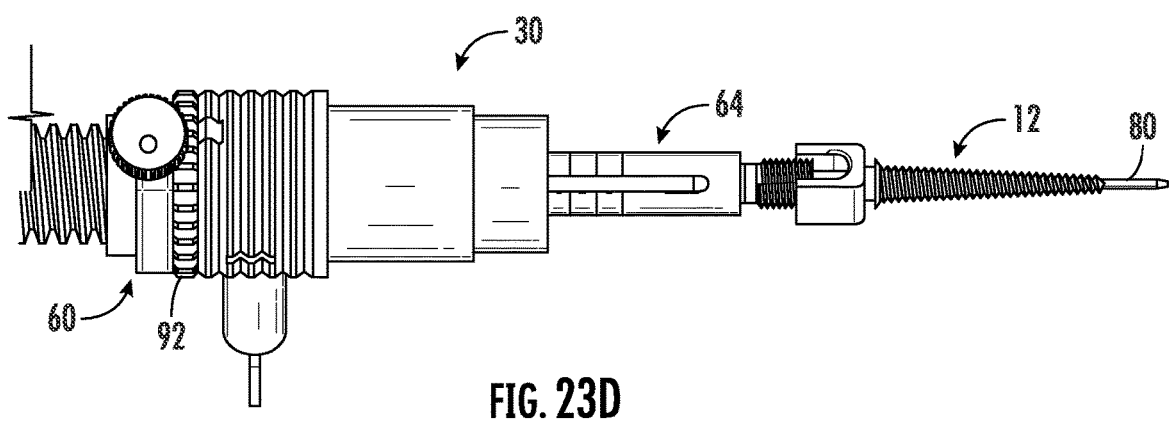
Figure 24A:
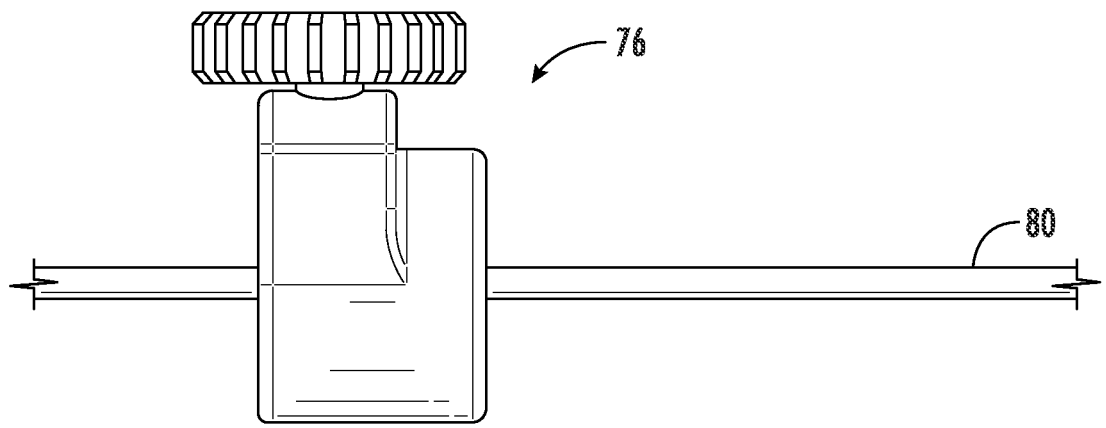
FIG. 24A illustrates the guidewire indicator coupled to the guidewire.
Figure 24B:
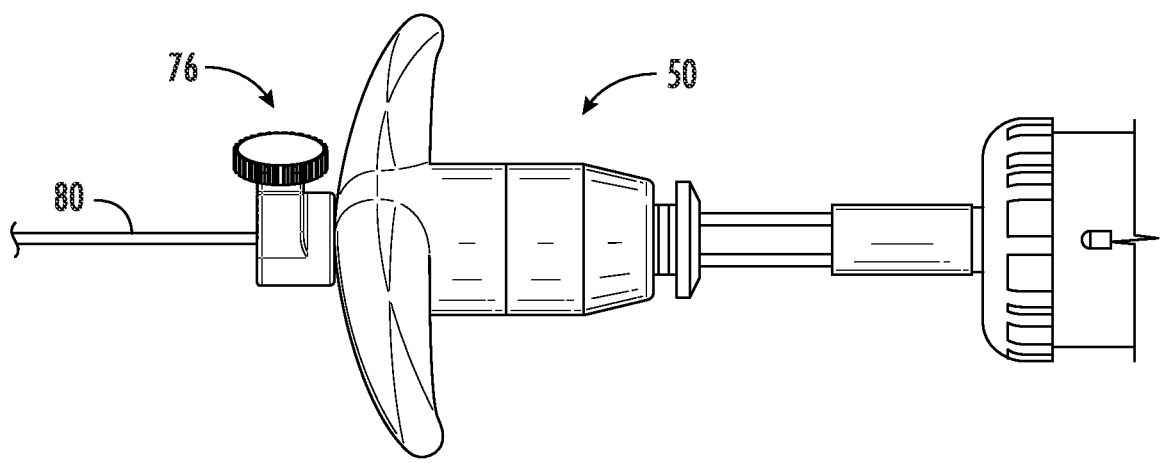
FIG. 24B illustrates the guidewire indicator and the proximal handle of the screwdriver.

As shown in FIG. 23D, if the physician wants the screw 12 to cover the guidewire 80 from the moment of tightening, then the distance Y must be zero, i.e., retaining device 60 is placed in contact with insert 92 before support barrel assembly 30 is fixed in position relative to the target site on the patient. If the physician wants the guidewire 80 to advance with the screw 12 for some distance Y prior to covering the guidewire 80, then the physician ensures that there is space between retaining device 60 and insert 92 before support barrel assembly 30 is fixed in position relative to the target site on the patient. Visual indicator 64 provides a visual reference point for the physician to determine this distance (see FIG. 23C). For example, visual indicator may include visual marks, colors, letters, numbers or other indicia on the distal end portion of central shaft 22 that define discrete distances, e.g., 5 mm, that allow the physician to know the exact distance of Y. In one such example, the guidewire 80 will progress with screw 12 for about 10 mm when only one mark is visible (see FIG. 23C). In another example, the guidewire 80 will not progress with the screw when all of the marks are visible (see FIG. 23D).

Once the distance Y is set by the physician, the screw 12 can be tightened into the tissue by rotating proximal handle 50. As the screwdriver 20 rotates relative to screw barrel 90, retaining device 60 will progress distally with central shaft 22 until it abuts against insert 92. At this point, inner threads 141 of insert 92 will press against curved portion 139 of spring tab 135 to allow retaining device 60 to move freely through lateral groove 140 and back into central groove 62. Once retaining device 60 is within central groove 62, it may move relative to central shaft 22 along central groove 62. Thus, as the screwdriver 20 continues to advance distally, retaining device 60 will remain fixed in position relative to screw barrel assembly 30. Since guidewire 80 is attached to retaining device 60, guidewire 80 will also remain fixed in position such that screw 12 covers guidewire 80 (see FIGS. 25A-25C).

Figure 25A:
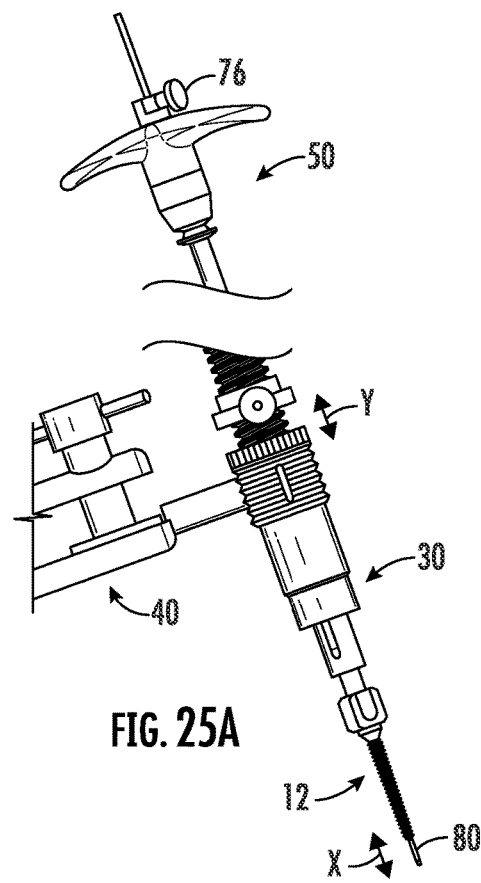
FIGS. 25A-25C illustrate a method of implanting a cannulated screw with the system of FIG. 1.
Figure 25B:
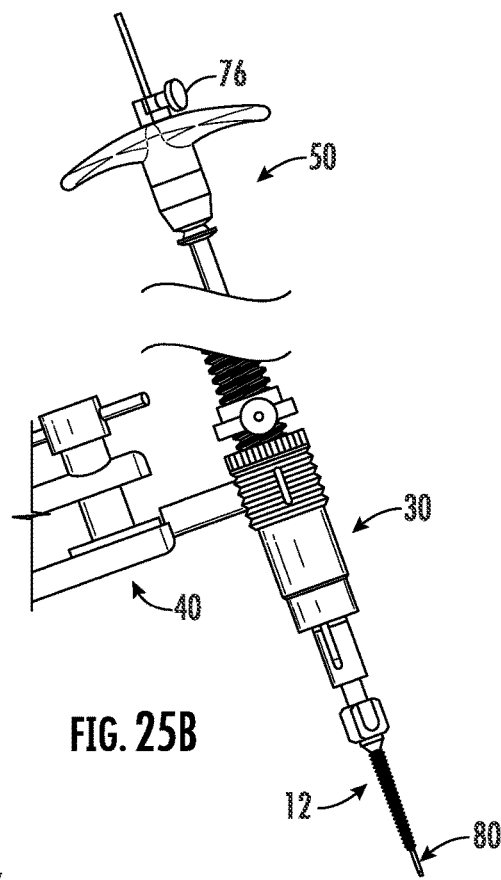
Figure 25C:
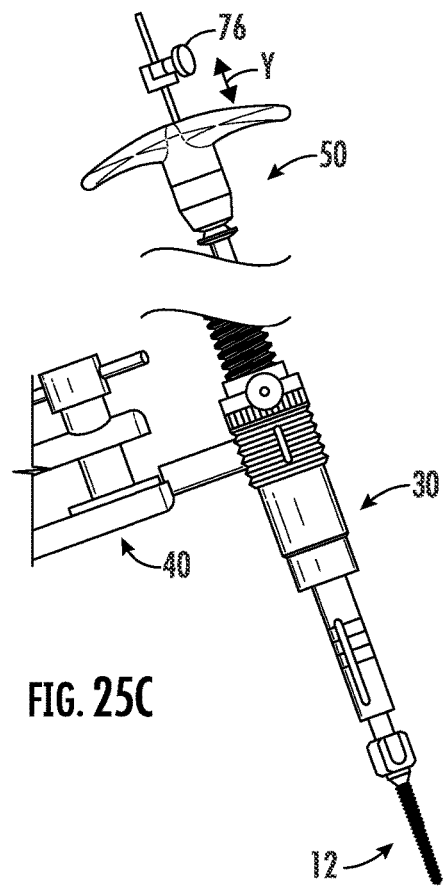

Guidewire indicator 76 provides confirmation that guidewire 80 is being covered by screw 12. As shown in FIGS. 25A-25C, so long as guidewire indicator 76 remains in contact with proximal handle 50, guidewire 80 is advancing with screw 12 (FIGS. 25A and 25B) However, as soon as guidewire indicator 76 moves proximally relative to handle 50 (or handle 50 moves distally relative to guidewire indicator 76), then guidewire indicator is no longer in contact with handle 50 and guidewire 80 is being covered by screw 12 (FIG. 25C).

Once screw 12 has been implanted, the physician may decouple screwdriver 20 from screw 12. To do so, proximal cap 66 is rotated relative to proximal head 65 such that cap 66 disengages from head 65 (see FIG. 26). Central shaft 22 includes a notch 160 that should remain visible when cap 66 is rotated away from head 65. If notch 160 is visible, then mating feature 204 may be rotated to disengage screwdriver 20 from screw head 200. If the notch 160 is not visible when cap 66 is rotated, then support arm 40 must first be unlocked from support barrel 90 to release screwdriver 20 from its constraints. Once notch 160 becomes visible again, then mating feature 204 may be disengaged from screw head 200.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the description. Accordingly, the description is intended to embrace all such alternatives, modifications, and variances. As well, one skilled in the art will appreciate further features and advantages based on the above-described embodiments. Accordingly, this description is not to be limited by what has been particularly shown and described, except as indicated by the appended claims.

What is claimed is:

1. A device for advancing a screw into tissue, the device comprising:
    a screwdriver having a central shaft with a longitudinal axis and a distal end configured for attachment to a screw and an inner lumen for receiving a guidewire;
    a retaining device for holding the guidewire fixed relative to the screw as the screw is advanced in a distal direction, wherein the retaining device is movably coupled to an outer surface of the central shaft and comprises a first locking element for fixing a position of the guidewire within the central shaft of the screwdriver, wherein the central shaft comprises a second locking element for fixing a longitudinal position of the retaining device relative to the central shaft; and
    a release device for releasing the guidewire from the screw and holding the guidewire fixed relative to the longitudinal axis as the screw is advanced in the distal direction, wherein the release device comprises a release member for releasing the second locking element and allowing the retaining device to move in a longitudinal direction relative to the central shaft, wherein the central shaft comprises a longitudinal groove and the retaining device comprises a pin configured to move through the longitudinal groove.

2. The device of claim 1, wherein the release device is configured to allow the guidewire to advance with the screw a fixed distance in the distal direction.

3. The device of claim 2, further comprising a visual indicator of the fixed distance.

4. The device of claim 1, wherein the longitudinal groove includes a lateral groove, wherein the pin is configured to move through the lateral groove to rotate the retaining device relative to the central shaft.

5. The device of claim 4, further comprising a spring tab on the central shaft for locking the retaining device within the lateral groove.

6. The device of claim 1, wherein the first locking element comprises a pin extending into the inner lumen of the central shaft and configured to engage the guidewire.

7. The device of claim 6, wherein the retaining member further comprises a rotatable knob coupled to the pin such that rotation of the knob moves the pin inwardly towards the inner lumen of the central shaft.

8. The device of claim 1, wherein the longitudinal groove comprises an inner portion and an outer portion, wherein the inner portion has side surfaces that are substantially parallel to each other, wherein the outer portion has side surfaces that extend away from each other in a lateral direction relative to the central shaft.

9. The device of claim 8, wherein the side surfaces of the outer portion form an angle of about 5 degrees to about 20 degrees with the side surfaces of the inner portion.

10. The device of claim 1, further comprising a screwing barrel having an internal lumen for receiving the central shaft of the screwdriver.

11. The device of claim 10, wherein the retaining device has an outer diameter larger than a diameter of the screwing barrel.

12. The device of claim 11, further comprising an insert configured for advancement into the internal lumen of the screw barrel, wherein the insert comprises a proximal end configured for attachment to a proximal end of the screw barrel.

13. The device of claim 12, further comprising a spring tab on the central shaft for locking the retaining device within the lateral groove, wherein the insert comprises a proximal release surface configured to engage the spring tab and release the retaining device when the retaining device engages the proximal end of the insert.

14. The device of claim 13, wherein the proximal release surface comprises an internal thread within the insert.

15. The device of claim 10, further comprising a support arm for supporting the screwing barrel at a fixed distance and orientation from a surface of the patient's skin.

16. The device of claim 15, further comprising a robotic control system coupled to the support arm.

17. The device of claim 10, wherein the central shaft has an outer thread and the screwing barrel has an inner thread for rotatably engaging the outer thread of the central shaft.

18. The device of claim 17, wherein the screw comprises a threaded shaft and wherein the inner and outer threads have substantially the same pitch as the threaded shaft.

19. The device of claim 17, wherein at least a portion of the outer thread of the central shaft is flattened to limit contact between the inner and outer threads as the screwdriver is rotated relative to the screw barrel.

20. The device of claim 1, wherein the retaining device comprises a substantially annular member disposed around the central shaft of the screwdriver, the device further comprising an outer ring coupled to the retaining member.

21. The device of claim 1, wherein the screw is a bone screw and the tissue is bone.

22. A system for advancing a cannulated screw into tissue, the system comprising:
 a screwdriver having a central shaft with a longitudinal axis, an outer thread, a distal end configured for attachment to a screw and an inner lumen for receiving a guidewire;
 a support barrel having an inner thread for rotatably engaging the outer thread of the screwdriver;
 a support arm for fixing the support barrel in position relative to a patient;
 a retaining device for holding the guidewire fixed relative to the screw as the screw is advanced in a distal direction, wherein the central shaft includes a retainer for fixing the retaining device relative to the central shaft, wherein the retainer comprises a spring tab within the central shaft and the proximal surface comprises an internal thread within the support barrel, and wherein the support barrel has a proximal surface configured to engage the retaining device and release the retaining device from the central shaft; and
 a release device for releasing the guidewire from the screw and holding the guidewire fixed relative to the longitudinal axis as the screw is advanced in the distal direction.

23. The system of claim 22, wherein the retaining device comprises an annular ring coupled to an outer surface of the central shaft and movable in a longitudinal direction relative to the central shaft.

24. The system of claim 23, wherein the retaining device comprises a retention member for securing the guidewire to the retaining device such that the guidewire moves in a longitudinal direction with the retaining device.

25. The system of claim 22, wherein the support barrier has a larger outer diameter than the retaining device to prevent further distal movement of the retaining device.

26. The system of claim 22, wherein the release device is configured to allow the guidewire to advance with the screw a fixed distance in the distal direction.

27. The device of claim 26, further comprising a visual indicator of the fixed distance.

28. The device of claim 22, further comprising a robotic control system coupled to the support arm.

* * * * *